(12) United States Patent
Perret et al.

(10) Patent No.: US 8,921,594 B2
(45) Date of Patent: Dec. 30, 2014

(54) USE OF A PISTON REACTOR TO IMPLEMENT A PHOSGENATION PROCESS

(75) Inventors: Nicolas Perret, Saint-Alban-de-Roche (FR); Denis Revelant, Genas (FR)

(73) Assignee: Vencorex France, Saint-Priest (FR)

( * ) Notice: Subject to any disclaimer, the term of this patent is extended or adjusted under 35 U.S.C. 154(b) by 529 days.

(21) Appl. No.: 13/140,474

(22) PCT Filed: Dec. 18, 2009

(86) PCT No.: PCT/FR2009/052605
§ 371 (c)(1),
(2), (4) Date: Sep. 1, 2011

(87) PCT Pub. No.: WO2010/076515
PCT Pub. Date: Jul. 8, 2010

(65) Prior Publication Data
US 2011/0306786 A1    Dec. 15, 2011

(30) Foreign Application Priority Data

Dec. 18, 2008  (FR) ..................................... 08 58782

(51) Int. Cl.
*C07C 263/10*   (2006.01)
*B01J 19/24*    (2006.01)
*B01J 19/00*    (2006.01)

(52) U.S. Cl.
CPC ........... *B01J 19/2415* (2013.01); *C07C 263/10* (2013.01); *B01J 2219/00006* (2013.01); *C07C 2102/42* (2013.01); *C07C 2101/16* (2013.01); *B01J 19/0053* (2013.01); *B01J 2219/00108* (2013.01); *B01J 2219/0011* (2013.01)
USPC ........... 560/347; 560/330; 560/336; 560/338

(58) Field of Classification Search
None
See application file for complete search history.

(56) References Cited

U.S. PATENT DOCUMENTS

| | | | |
|---|---|---|---|
| 3,544,611 A | 12/1970 | Michelet et al. | |
| 3,552,933 A | 1/1971 | Jones et al. | |
| 4,096,165 A | 6/1978 | Meyers | |
| 4,096,214 A | 6/1978 | Percevaut et al. | |
| 4,422,976 A * | 12/1983 | Yamamoto et al. | 560/347 |
| 7,112,694 B2 | 9/2006 | Brodhagen et al. | |
| 2006/0025556 A1 | 2/2006 | Koch et al. | |

FOREIGN PATENT DOCUMENTS

| | | |
|---|---|---|
| CN | 1094395 A | 11/1994 |
| CN | 101184727 A | 2/2008 |
| DE | 10260094 | 7/2004 |
| FR | 1469105 | 2/1967 |
| FR | 2503146 | 10/1987 |
| GB | 1173890 | 3/1968 |
| WO | W02008055898 A1 | 5/2008 |

OTHER PUBLICATIONS

Chinese Office Action issued on Feb. 26, 2013.
PCT International Search Report for PCT/FR2009/052605 by EPO dated Mar. 17, 2010.

* cited by examiner

*Primary Examiner* — Sudhakar Katakam
(74) *Attorney, Agent, or Firm* — Michael B. Fein, Esq.; Eckert Seamans Cherin & Mellott, LLC

(57) ABSTRACT

A process for phosgenating an amine comprising employing a plug-flow type reactor with internal recycle is disclosed. The process can be continuous, which makes it possible to prepare, in a single stage, a (poly)isocyanate with a good yield, without formation of byproducts and on simplifying the plant in order to carry out the process so as to promote safety.

11 Claims, 1 Drawing Sheet

USE OF A PISTON REACTOR TO IMPLEMENT A PHOSGENATION PROCESS

CROSS-REFERENCE TO RELATED APPLICATIONS

The present application is a 35 U.S.C. 371 National Stage Application of International Application No. PCT/FR2009/052605, Filed Dec. 18, 2009, which claims priority under 35 U.S.C. §119(a) to France Application No. 0858782, Filed, Dec. 18, 2008, each of which is incorporated herein by reference in its entirety.

BACKGROUND OF THE INVENTION

The present invention relates to the use of a reactor of plug-flow type to carry out a phosgenation process.

The use of a reactor of plug-flow or tubular type to carry out phosgenation processes is described for example, in the patent FR 1 578 808.

The phosgenation process is sometimes carried out in several stages. Thus, the application US 2006/0025556 describes a two-stage phosgenation process, the first stage preferably being carried out under high temperature and high pressure in a reactor of adiabatic plug-flow type. The application DE 102 60 094 describes a phosgenation process under high temperature and high pressure with successive reduction of the reaction medium in pressure in a reactor and reactive columns. The U.S. Pat. No. 7,112,694 reports a phosgenation process under high temperature and high pressure in a cascade of reactors of plug-flow type. The multiplication in the number of stages and of reactors for implementing the phosgenation renders complex the phosgenation process and the plant for the implementation. It is also more difficult to ensure the safety of personnel in the light of the complexity of the plants and of the multiplication in the number of components of the plants comprising phosgene, which is highly toxic by inhalation.

The phosgenation processes of the prior art also exhibit other disadvantages: the reaction volumes are generally high and undesirable products are formed during the reaction, which, on the one hand, prevent the fluids from flowing by formation of residues in the reactors and the pipes and, on the other hand, result in a fall in yield of the phosgenation reaction.

The works Turbulent Mixing and Chemical Reactions (Jerry Baldyga & John R. Bourne) and Géenie de la réaction chimique conception at fonctionnement des réacteurs [Chemical Reaction Engineering: Design and Operation of Reactors] (J. Viilermaux) report that a reactor of plug-flow type is particularly suitable for carrying out reactions of competitive type (namely, when at least two reactions are in competition with respect to one another)/consecutive type (namely, when at least two reactions follow one another). In point of fact, the phosgenation reaction of an amine corresponds exactly to this scenario since the isocyanate formed can in its turn react competitively with the starting amine to form a byproduct of urea type which cannot be recovered in value:

R—NH$_2$+COCl$_2$→RNH—CO—Cl+
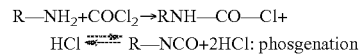 R—NCO+2HCl: phosgenation

R—NCO+R—NH$_2$→R—NH—CO—NH—R: competitive formation of urea

The abovementioned works teach that the plug-flow reactor without back mixing is particularly suitable for carrying out the phosgenation reaction.

This is because, in a reactor of plug-flow type without back mixing, the molecules reacting with one another move in a single direction. Thus, the product formed, namely the isocyanate, does not return to the reaction region where the amine occurs. Consequently, the reaction for the formation of urea due to the reaction between isocyanate and the amine is penalized.

SUMMARY OF THE INVENTION

One of the objectives of the present invention is to provide a continuous phosgenation process which makes it possible to prepare, in a single stage, a (poly)isocyanate with a good yield, without formation of byproducts and on simplifying the plant in order to carry out the process so as to promote safety.

The invention relates to the use of a reactor of plug-flow type with internal recycle for carrying out a process for the phosgenation of an amine.

In chemical engineering terminology, a flow is said to be of "plug-flow" type when the molecules reacting with one another move in a single direction: it is possible, in this case, to lay down an equivalence between the progress of the reaction and the distance travelled by the molecules since their injection.

The term "plug-flow with recycle" is understood to mean that the main stream of molecules reacting with one another is arranged according to a flow of plug-flow type and that a portion of this main stream is sent back from the downstream side to the upstream side, close to the region of initial injection of the molecules: the overall flow is always of plug-flow type, the initial concentrations of the molecules are weighted by the downstream stream.

The term "internal recycle" is understood to mean that the outlet stream from the reactor is sent back into the inlet stream inside the reactor of plug-flow type by virtue of the actual geometry of the reactor, without use of external mechanical means. The geometry of the reactor, namely the difference between the diameter of the reactor and the diameter of the jets of reactants, creates a region of recirculation or internal recycle. The geometry of the reactor makes it possible to combine recycle and rapid reaction. In particular, a reactor of plug-flow type with internal recycle is devoid of external recycle pipe, also known as recycling loop. The reactor employed in the invention is thus a closed system, which is an advantage in terms of safety.

The internal recycle differs from the external recycle in the components described below. An external recycle device comprises a pipe for recycling external to the reactor. A portion of the reaction medium exiting from the reactor is recycled by means of this external recycling pipe. The reaction medium can optionally be subjected to stages of separation before being recycled (for example by using a gas separator). Thus, the patent application FR 1 469 105 describes a two-stage phosgenation process, the first stage being carried out under pressure in a reactor plug-flow type with external recycle and the second stage being carried out after reduction of the reaction medium in pressure in a reactive column. Likewise, the patent application FR 2 503 146 describes a two-stage phosgenation process in which one of the stages or both stages can be carried out in a tubular recycling pipe corresponding to an external recycle.

The term "phosgenation" denotes the reaction of phosgene (COCl$_2$) with an amine to produce a (poly)isocyanate through the intermediacy of a carbamoyl chloride.

The term "amine" denotes a molecule comprising at least one primary, secondary or tertiary amine functional group. The amine can be aliphatic, cyclic or aromatic.

The inventors have demonstrated that the use of a reactor of plug-flow type with internal recycle is particularly suitable for carrying out a process for the phosgenation of an amine. This is because this type of reactor makes it possible to minimize the phosgenation reaction time and thus to minimize the formation of undesirable byproducts and to increase the yield of the phosgenation reaction.

The invention also relates to a process for the continuous preparation of a (poly)isocyanate comprising a stage of the phosgenation reaction of an amine in a reactor of plug-flow type with internal recycle.

The term "continuous preparation" is understood to mean that the preparation of the (poly)isocyanate is carried out with continuous injection of reactants into the reactor.

The term "(poly)isocyanate" is understood to mean an isocyanate, that is to say a molecule comprising one isocyanate functional group, or a polyisocyanate, that is to say a molecule comprising at least two isocyanate functional groups.

DETAILED DESCRIPTION

Figure 1:
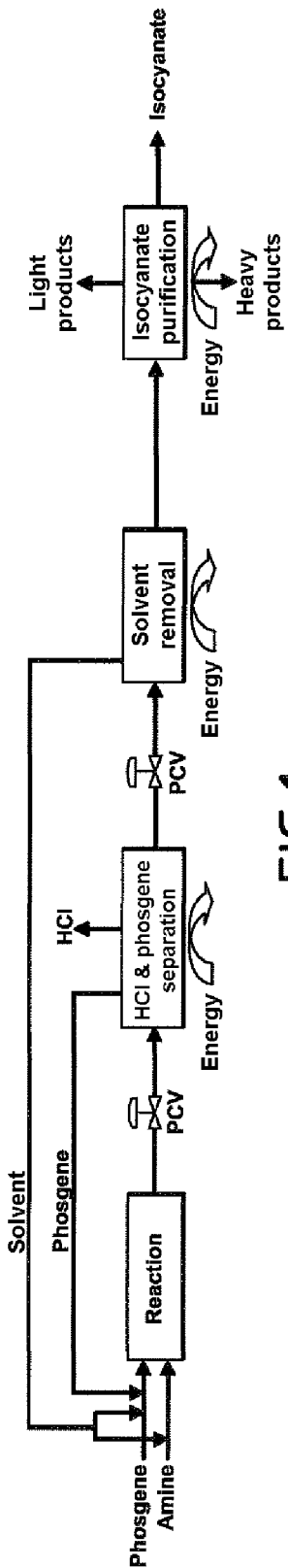
FIG. 1 is a general diagram of the plant.

In one embodiment, the process for the continuous preparation of a (poly)isocyanate according to the invention comprises the stages consisting in:
a) injecting an amine and phosgene into a reactor of plug-flow type with internal recycle, and
b) carrying out the phosgenation reaction of said amine in said reactor of plug-flow type with internal recycle.

Preferably, the phosgene is introduced in a super-stoichiometric amount (that is to say, in excess) with respect to the amine.

In one embodiment, in the process for the continuous preparation of a (poly)isocyanate according to the invention, the duration of the phosgenation reaction of stage b) is less than 200 ms, in particular less than 100 ms, preferably less than 50 ms and more preferably still less than 15 ms.

The reactor of plug-flow type with internal recycle advantageously makes it possible to minimize the duration of the phosgenation reaction and thus to minimize the formation of undesirable byproducts.

The term "duration of the phosgenation reaction" denotes the time necessary between the moment when the amine enters the reactor (brought into contact with the phosgene) and the moment when the amine has been completely converted.

During the phosgenation reaction, the interior of the reactor of plug-flow type comprising internal recycle employed can be broken down into two distinct regions (which are not physically separated from one another), in which the flow is different:
  a first stirred region with internal recycle,
  a second region of flow of plug-flow type.

The first region is a stirred region, the stirring originating from the internal recycle due to the geometry of the reactor. The streams of amine and phosgene suddenly change direction on arriving in the reactor, due to the geometry of the reactor, which brings about the internal recycle. In this first region with internal recycle, the amine and the phosgene are converted to carbamoyl chloride according to the following reaction:

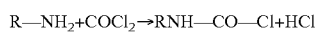

In the second region, the flow is of plug-flow type and the molecules move in a single direction. In this second region, the carbamoyl chloride is converted to isocyanate according to the following reaction:

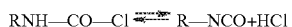

The reaction of the amine with the phosgene takes place mainly in the first region of flow of plug-flow type with internal recycle, in a region very close to the point of the reactor where the amine and phosgene reactants meet. The reaction region is defined by the volume in which the mixing of reactants and the complete conversion of the amine take place. At the outlet of the reaction region, the exiting stream is composed of excess phosgene and of (poly) isocyanate and/or of carbamoyl chloride (hydrochlorinated form of the isocyanate), the carbamoyl chloride generally being predominant with respect to the (poly)isocyanate. The concentration of amine in the exiting stream is virtually zero as all the amine was converted during the phosgenation reaction. This exiting stream is, for one part, discharged downstream of the reactor in the region of flow of plug-flow type and, for another part, sent back by back mixing to the reaction region by virtue of the internal recycle. The arrival of this exiting stream in the reaction region thus makes it possible to locally increase the flow rate of phosgene in the reaction region. The stoichiometric excess of phosgene with respect to the amine is thus locally higher in the reaction region than elsewhere in the plug-flow reactor. The increase in the stoichiometric ratio of phosgene promotes the conversion of the amine and thus the phosgenation reaction.

As the phosgenation reaction is exothermic, the temperature of the streams exiting from the reaction region is higher than the temperature of the streams entering this region (that is to say, the streams of amine and of phosgene which are injected into the reactor). The stream exiting from the reaction region sent back to the reaction region by the back mixing by virtue of the internal recycle thus makes it possible to increase the temperature of the reaction region, which promotes the phosgenation kinetics.

The arrival of this additional recycle stream promotes the micromixing of the reactants in the reaction region and thus promotes the phosgenation reaction.

Furthermore, the reduction in the amount of undesirable byproducts can be explained as follows. The concentration of undesirable byproducts is proportional to the product of the amine concentration and of the (poly)isocyanate concentration. Insofar as the stoichiometric excess of phosgene is increased locally in the reaction region by the part of the exiting stream which is sent back to the reaction region by virtue of the internal recycle, the concentration of amine is thus locally lower and the concentration of byproducts also.

The reduction in the amount of undesirable byproducts can also be explained by the fact that the recycle is internal. This is because, during a phosgenation reaction, the composition of the recycled reaction medium is not the same when an internal or external recycle is carried out.

More specifically, generally, when a system with external recycle is used, the reaction medium at the outlet of the reactor is recycled and reinjected upstream of the reactor via an external pipe. The reaction medium at the outlet of the reactor comprises, in addition to the excess phosgene, predominantly isocyanate. In point of fact, when the isocyanate is reinjected upstream of the reactor, it is capable of reacting with the incoming amine to form the urea (reaction for the formation of urea in competition with the formation of the carbamoyl chloride).

In contrast, when a system with internal recycle is used, the reaction medium from the first region of flow of plug-flow type with internal recycle is sent back downstream of the reactor. In point of fact, this reaction medium comprises more carbamoyl chloride than isocyanate. The carbamoyl chloride is a form of isocyanate which is rendered inert by a molecule of HCl and which is much less reactive with regard to the amine than the isocyanate itself. Thus, the side reaction for formation of the urea is penalized to the advantage of the reaction for formation of the carbamoyl chloride (which will be converted to isocyanate in the second region of the reactor).

Furthermore, the recycle is much faster with a reactor comprising internal recycle than with a reactor comprising external recycle. In point of fact, the faster the rate of recycle, the more the formation of byproducts is minimized.

The formation of byproducts is thus penalized with an internal recycle and the isocyanate yields are thus improved with respect to an external recycle. Thus, a reactor comprising internal recycle is more suitable for the phosgenation reaction, which is of competitive type (competition with the formation of urea) and consecutive type, than a reactor comprising external recycle.

Thus, the process according to the invention makes it possible to obtain complete conversions of amine (that is to say that all the amine reacts) and yields of (poly)isocyanate, after isolation and purification, of greater than 90%, preferably greater than 95%.

Generally, the reactor of plug-flow type with internal recycle is devoid of internal walls and of internal compartments. This is because internal compartments are not necessary for internal recycle to take place. Furthermore, it is preferable to avoid internal compartments being present in a reactor employed in a phosgenation reaction, which is a reaction for which the reaction medium is highly corrosive (mainly because of the presence of phosgene and hydrochloric acid), which results in fouling of the walls.

In a preferred embodiment, in the process for continuous preparation of a (poly)isocyanate according to the invention, the reactor of plug-flow type with internal recycle comprises a tubular part preceded by a divergent.

The term "tubular part" denotes the tube of the plug-flow reactor.

The term "divergent" denotes an increasing variation in diameter of the reactor in the inlet region for the reactants. It is thus possible to have a tubular part with a diameter $d1$, followed by a cone and by a second tubular part with a diameter $d2$ with $d1<d2$, or directly a conical part, at the vertex of which the reactants are introduced, followed by a tubular part with a large diameter.

The divergent thus creates the internal recycle and thus the advantages demonstrated above of the internal recycle.

In a preferred embodiment, in stage a) of the process for the continuous preparation of a (poly)isocyanate according to the invention, the amine and the phosgene are injected by a system comprising impinging jets.

The term "system comprising impinging jets" denotes a system which makes it possible to introduce the amine and the phosgene in the form of convergent liquid and/or gaseous and/or supercritical jets into the reactor.

Preferably, in stage a) of the process for the continuous preparation of a (poly)isocyanate according to the invention, the system comprising impinging jets is characterized by an angle between the jet(s) of the amine and the jet(s) of the phosgene of from 5 to 85°, in particular from 15 to 70° and preferably from 20 to 50°.

This is because such angles are particularly suitable for minimizing the phosgenation reaction time.

According to a preferred embodiment, the abovementioned system comprising impinging jets is characterized by:
  an amine impinging jet speed of from 20 to 80 m/s, in particular from 25 to 70 m/s and preferably from 30 to 60 m/s, and
  a speed for the impinging jet of the phosgene of from 10 to 100 m/s, in particular from 20 to 90 m/s and preferably from 30 to 80 m/s.

This is because such speeds are particularly suitable for minimizing the phosgenation reaction time.

Preferably, the system comprising impinging jets is characterized in that it comprises injection orifices chosen from circular holes or holes comprising a variation in curvature of elliptical type or star-shaped holes, so as to increase the wetted perimeter/hydraulic diameter ratio.

The term "injection orifice" denotes the opening of the reactor which makes it possible to inject the amine or the phosgene therein.

The greater the external surface area of the jets of reactants, the better the exchange which takes place between the reactants and the more the phosgenation reaction time is minimized. Elliptical holes or star-shaped holes are thus better suited than circular holes, for which the exchange surface area is the lowest.

In one embodiment of the process according to the invention, the internal recycle is obtained by injection of the reactants through the divergent and the ratio of the diameter of the reactor to the diameter of the jets is from 3 to 100, in particular from 10 to 80 and preferably from 20 to 60.

The term "diameter of the reactor" denotes the internal diameter of the tube of the plug-flow reactor.

The term "diameter of the jets" denotes the mean diameter of the jets of reactant (of amine or of phosgene). If the injection orifice is a circular hole, this diameter corresponds to the diameter of the circular hole. For the other types of injection orifice, the jet diameter corresponds to the mean diameter of the injection orifice.

In one embodiment of the process according to the invention, the divergent has a conical shape with an angle of from 7 to 90°, in particular from 15 to 80° and preferably from 25 to 75° and the injection orifices are at the vertex of the divergent.

The internal recycle can mainly be improved by adjusting the ratio of the diameter of the reactor to the diameter of the jets and/or the angle of the divergent. The speeds of the amine and phosgene impinging jets have little effect on the quality of the internal recycle.

In one embodiment of the process according to the invention, the ratio of the molar amount of phosgene to the molar amount of amine is greater than 2 and preferably greater than 4.

This is because these molar ratios are particularly suitable for converting all of the amine into poly(isocyanate).

In one embodiment of the process according to the invention, the amine and/or the phosgene is pure or is in solution in a solvent, such as monochlorobenzene, ortho-dichlorobenzene or any solvent which is, on the one hand, capable of dissolving the amine and the phosgene and, on the other hand, unreactive with the amine and the phosgene (inert solvent). The phosgene, when it is used pure, can be in the liquid or super-critical form.

In one embodiment of the process according to the invention, the temperature in the reactor of plug-flow type is from 100 to 300° C., in particular from 120 to 250° C. and preferably from 135 to 230° C.

In one embodiment of the process according to the invention, the pressure in the reactor of plug-flow type with internal recycle is from 5 to 100 bar, in particular from 10 to 80 bar and preferably from 20 to 70 bar. These high pressures are particularly suitable as they make it possible to keep the carbamoyl chloride in this "inerted" form and to prevent the conversion thereof to (poly)isocyanate in the first region of flow of plug-flow type with internal recycle, which prevents the formation of byproducts, as explained above.

In one embodiment of the process according to the invention, the isocyanate is chosen from tetra-, penta-, hexa- or octamethylene diisocyanate, toluene diisocyanate, isophorone diisocyanate, norbornane diisocyanate, lysine diisocyanate, lysine triisocyanate and 1,5-naphthylene diisocyanate.

In one embodiment of the process according to the invention, the amine is chosen from 1,4-butylenediamine, 1,5-pentylenediamine, 1,6-hexamethylenediamine, 1,8-octamethylenediamine, toluenediamine, isophoronediamine, norbornanediamine, lysinediamine, lysinetriamine and 1,5-naphthylenediamine.

The invention will be understood in more detail by means of the following figures and examples.

Figure 2:
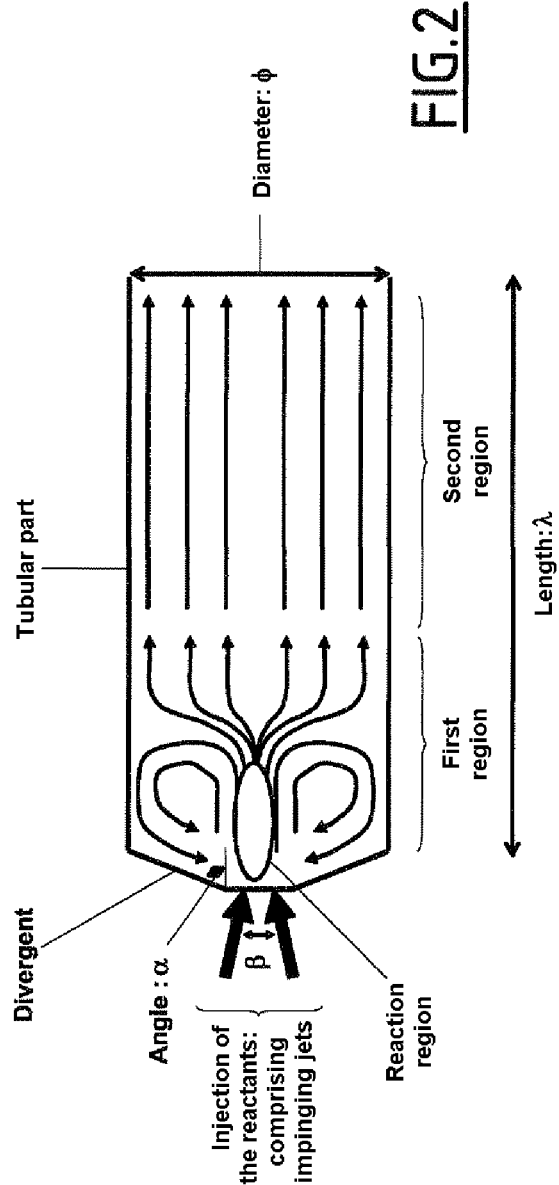
FIG. 2 is a diagram of the reactor of plug-flow type with internal recycle and divergent.

FIG. 1: General diagram of the plant.
FIG. 2: Diagram of the reactor of plug-flow type with internal recycle and divergent.

EXAMPLES

Example 1

150 kg/h of a solution of hexamethylenediamine diluted to 15% by weight in monochlorobenzene and 250 kg/h of a solution of phosgene diluted to 75% by weight in monochlorobenzene are cointroduced, by means of an injection system comprising impinging jets, into a heat-insulated reactor of plug-flow type with internal recycle (cf. FIG. 2) defined by a length $\lambda=2$ m, a diameter $\phi=7.5$ cm and a divergent angle $\alpha=25°$. The solutions of reactants are conveyed by means of high pressure pumps; the temperature of the hexamethylenediamine solution is 145° C. and that of the phosgene solution is 180° C. The injection system makes it possible to bring the jets of reactants into contact with an angle $\beta$ of 25° with jet speeds respectively of 40 m/s for the amine solution and 60 m/s for the phosgene solution. The pressure in the reactor is regulated at 40 bar by means of a pressure control valve (PCV) and the resulting mean temperature is 185° C. After reducing this reaction medium in pressure, removing the HCl formed and the excess phosgene and then purifying the hexamethylene diisocyanate, a conversion yield of 97% by weight is obtained.

Example 2

300 kg/h of a solution of toluenediamine diluted to 18% by weight in ortho-dichlorobenzene and 500 kg/h of a solution of phosgene diluted to 75% by weight in ortho-dichlorobenzene are cointroduced, by means of an injection system comprising impinging jets, into a heat-insulated reactor of plug-flow type with internal recycle (cf. FIG. 2) defined by a length $\lambda=3$ m, a diameter $\phi=5$ cm and a divergent angle $\alpha=20°$. The solutions of reactants are conveyed by means of high-pressure pumps; the temperature of the toluenediamine solution is 125° C. and that of the phosgene solution is 100° C. The injection system makes it possible to bring the jets of reactants into contact with an angle $\beta$ of 35° with jet speeds respectively of 30 m/s for the amine solution and 40 m/s for the phosgene solution. The pressure in the reactor is regulated at 35 bar by means of a pressure control valve (PCV) and the resulting mean temperature is 145° C. After reducing this reaction medium in pressure, removing the HCl formed and the excess phosgene and then purifying the toluene diisocyanate, a conversion yield of 98% by weight is obtained.

What is claimed is:

1. A process for phosgenating an amine comprising phosgenating said amine with phosgene in plug-flow type reactor with internal recycle, the reactor comprising a first region with internal recycle followed by a second region of plug-flow type, wherein the first region comprises a system of impinging jets and wherein the reactor has a diameter and the impinging jets have a diameter and the ratio of the diameter of the reactor and the diameter of the jets is from 3 to 100.

2. A process for continuous preparation of a (poly)isocyanate, comprising
   a) injecting an amine and phosgene into a reactor of plug flow type with internal recycle, the reactor comprising a first region with internal recycle followed by a second region of plug-flow type, wherein the first region comprises a system of impinging jets and wherein the reactor has a diameter and the impinging jets have a diameter and the ratio of the diameter of the reactor and the diameter of the jets is from 3 to 100;
   b) carrying out the phosgenation reaction of said amine in said a reactor of plug-flow type with internal recycle.

3. The process for the continuous preparation of a (poly)isocyanate of one of claim 2 in which the duration of the phosgenation reaction of stage b) is less than 200 ms.

4. The process for the continuous preparation of a (poly)isocyanate of claim 2 in which the reactor of plug-flow type with internal recycle comprises a tubular part preceded by a divergent.

5. The process for the continuous preparation of a (poly)isocyanate of claim 2 wherein in step a) the amine and the phosgene are injected by a system comprising impinging jets.

6. The process for the continuous preparation of a (poly)isocyanate of claim 5 in which the system comprising impinging jets is characterized by an angle between the impinging jet of the amine and the impinging jet of the phosgene of from 5 to 85° and/or by an amine impinging jet speed of from 20 to 80 m/s and a speed for the impinging jet of the phosgene of from 10 to 100 m/s.

7. The process for the continuous preparation of a (poly)isocyanate of claim 4 in which the internal recycle is obtained by injection of the reactants through the divergent and the ratio of the diameter of the reactor to the diameter of the jets is from 3 to 100.

8. The process for the continuous preparation of a (poly)isocyanate of claim 7 in which the divergent has a conical shape with an angle of from 7 to 90° and the injection orifices are at the vertex of the divergent.

9. The process for the continuous preparation of a (poly)isocyanate of claim 2 in which the temperature in the reactor of plug-flow type is from 100 to 300° C. and/or the pressure in the reactor of plug-flow type with internal recycle is from 5 to 100 bar.

10. The process for the continuous preparation of a (poly)isocyanate of claim 2 in which the isocyanate is chosen from tetra-, penta-, hexa- or octamethylene diisocyanate, toluene diisocyanate, isophorone diisocyanate, norbornane diisocyanate, lysine diisocyanate, lysine triisocyanate and 1,5-naphthylene diisocyanate.

11. The process according to claim 3 wherein the duration of the phosgenation reaction of stage b) is less than 15 ms.

* * * * *